United States Patent

Takakarhu et al.

[11] Patent Number: 5,602,348
[45] Date of Patent: Feb. 11, 1997

[54] METHOD AND EQUIPMENT FOR TAKING A SAMPLE

[75] Inventors: Jouni Takakarhu, Helsinki; Klaus Nyfors, Porvoo, both of Finland

[73] Assignee: Borealis Polymers Oy, Porvoo, Finland

[21] Appl. No.: 553,363

[22] PCT Filed: May 10, 1994

[86] PCT No.: PCT/FI94/00182

§ 371 Date: Feb. 12, 1996

§ 102(e) Date: Feb. 12, 1996

[87] PCT Pub. No.: WO94/27134

PCT Pub. Date: Nov. 24, 1994

[30] Foreign Application Priority Data

May 12, 1993 [FI] Finland .................................. 932159

[51] Int. Cl.⁶ .................................................. B01F 3/04
[52] U.S. Cl. .................................. 73/864.81; 73/19.1
[58] Field of Search ........................... 73/863.23, 863.24, 73/863.41, 863.83, 863.86, 864.81, 19.02, 19.1, 19.11, 19.12, 864.34, 863.71

[56] References Cited

U.S. PATENT DOCUMENTS

| | | | |
|---|---|---|---|
| 3,556,730 | 1/1971 | Mitacek | 23/230 |
| 3,616,272 | 10/1971 | Goerg et al. | 204/1 T |
| 4,517,135 | 5/1985 | Szerenyi et al. | 73/19.1 |
| 4,735,779 | 4/1988 | Handel | 422/105 |
| 4,800,761 | 1/1989 | Spencer | 73/863.71 |
| 4,942,135 | 7/1990 | Zaromb | 73/863.23 |
| 5,180,558 | 1/1993 | Takakarhu et al. | 422/131 |

FOREIGN PATENT DOCUMENTS

| | | |
|---|---|---|
| 0460594 | 12/1991 | European Pat. Off. |
| 1648870 | 5/1971 | Germany |
| 1257964 | 12/1971 | United Kingdom |
| 8100766 | 3/1981 | WIPO |

*Primary Examiner*—Robert Raevis
*Attorney, Agent, or Firm*—Steinberg, Raskin & Davidson, P.C.

[57] ABSTRACT

The invention concerns a method and an equipment for taking a sample in slurry polymerization. The sample is taken directly from the liquid phase of the reactor (15) through an in-line filter (40). The slurry flow is maintained in the in-line filter (40) at a sufficiently hight level to prevent immobilization of polymer or catalyst particles on the filter face of the in-line filte (40).

3 Claims, 2 Drawing Sheets

METHOD AND EQUIPMENT FOR TAKING A SAMPLE

The invention concerns a method and an equipment for taking a sample in slurry polymerization.

Various methods have been developed for the preparation of solid and semisolid polymers out of hydrocarbons, such as 1-olefins. In one such method, olefins, such as ethylene, propylene, butylene, or pentenes, are polymerized in the presence of catalysts in hydrocarbon diluents or while the monomers themselves act as diluents. In such a case, the reaction agents are kept in the solution phase by maintaining a suitable pressure in the polymerization reactor. When the polymer that is formed is insoluble or poorly soluble in said diluent, the polymer product is formed as particles and, thus, the product flow comprises a suspension composed of polymer particles, diluents, and monomers. This product flow is usually passed into a polymer separation tank, in which the solid materials and the liquid and gaseous constituents are separated from one another.

One reactor type that is applied in such methods is a continuous pipe reactor that forms a loop, the polymerization taking place in a turbulent flow circulating in the loop. The product, which contains a polymer, diluents and monomers, is taken out of the loop reactor either continuously or, more commonly, periodically through an exhaust valve, being passed into a separator, in which the polymer is separated by lowering the pressure.

In view of regulation of the polymerization reaction, samples can be taken from the product flow of the reactor continuously or periodically. A normal way is to take a sample from the gas flow departing from the polymer separation tank and to analyze this gas sample by various methods, for example by means of gas chromatography. Such an arrangement is described, e.g., in the U.S. Pat. No. 3,556,730.

In this prior-art procedure, the period of delay that occurs from the departure of the product from the polymerization reactor until the time of start of the analysis is often considerably long, and during that period essential changes may take place in the process. Thus, the sample is not representative at all times. Therefore, it would be preferable to make said period of delay of analysis shorter.

In the FI Patent No. 85,191, a method is described by whose means a substantial shortening of the sampling delay is achieved. In said method, the sample is taken from the product pipe through a closing valve of the on/off type, which valve is closed for the time of the pressure swing produced on opening of the exhaust valve, and which valve is opened after said pressure swing.

In a polymerization plant, the process delay related to the analysis is, as a rule, of an order of about 10 minutes. When a sampling system in accordance with the FI Patent 85,191 is used, the process delay related to the analysis is shortened to about one minute under equivalent conditions.

For the regulation of the properties of the polymer in slurry polymerization, precise regulation of the concentration is required. Conventionally this has been carried out by analyzing the input concentration, in mixing-tank reactors the gas-phase concentrations or the concentrations of the gas phase separated from the product. These measurements do, however, not give sufficiently precise information on the liquid-phase concentrations in the reactor.

When the input concentration is analyzed, the factual concentrations in the reactor are not known. When the gas-phase concentrations in a mixing-tank reactor are analyzed, the factual liquid-phase concentrations are not known. Further, problems are produced by the adhesion of polymer particles in the sampling system. When the taking of samples takes place from the gas flow after the product pipe of the reactor (after the separation tank), adhering of polymer particles in the sampling line causes problems. Further, possible return-blow gases in the product filters may interfere with the analyzing, and there may be a long time delay until the analysis of concentration has been carried out. Also, analyzing from the gas space is impossible if the polymer slurry is fed from one reactor into another without separation of gases. An analysis directly from the slurry by means of a conventional filter is not possible, because the filter is under reaction conditions and, if small catalyst particles remain on the face of the filter, said particles continue the polymerization on the filter and block the filter rapidly.

The object of the present invention is to provide a method and an equipment which permit taking of samples without any substantial delays and in which the problems arising from adhering of polymer particles have been eliminated. It is a further object of the invention to provide a method and an equipment which may also be applied to slurry reactors which are connected in series and in which there is no separation of polymer and liquid/gas between the reactors.

The method in accordance with the invention is characterized in that the sample is taken directly from the liquid phase of the reactor through an in-line filter, and that the slurry flow is maintained in the in-line filter at a sufficiently high level to prevent immobilization of polymer or catalyst particles on the face of the in-line filter.

The equipment in accordance with the invention is characterized in that the equipment comprises an in-line filter, which communicates with the liquid phase of the reactor by one of its ends by means of a first flow duct and by the other one of its ends by means of a second flow duct.

The method of analysis in accordance with the invention is carried out directly from the liquid phase in which the polymerization takes place, without any time delay and without problems of adhesion of particles. The in-line filter in accordance with the invention can also be accomplished with a minimal number of moving and wearing parts.

In the method in accordance with the invention, the in-line filter is washed by means of a slurry flow of a very high velocity, e.g. 3 ... 10 metres per second. In the case of the slurry-loop reactor, the difference in pressure across the pump of the loop reactor produces the necessary high-velocity flow in the pipe of the filter. In the case of a tank reactor, it is possible to use a slurry pump. If necessary, it is also possible to use reflux washing with an inert liquid to cleanse the filter.

The invention will be described in detail with reference to some preferred embodiments of the invention illustrated in the figures in the accompanying drawings, the invention being, however, not supposed to be confined to said embodiments alone.

Figure 1:
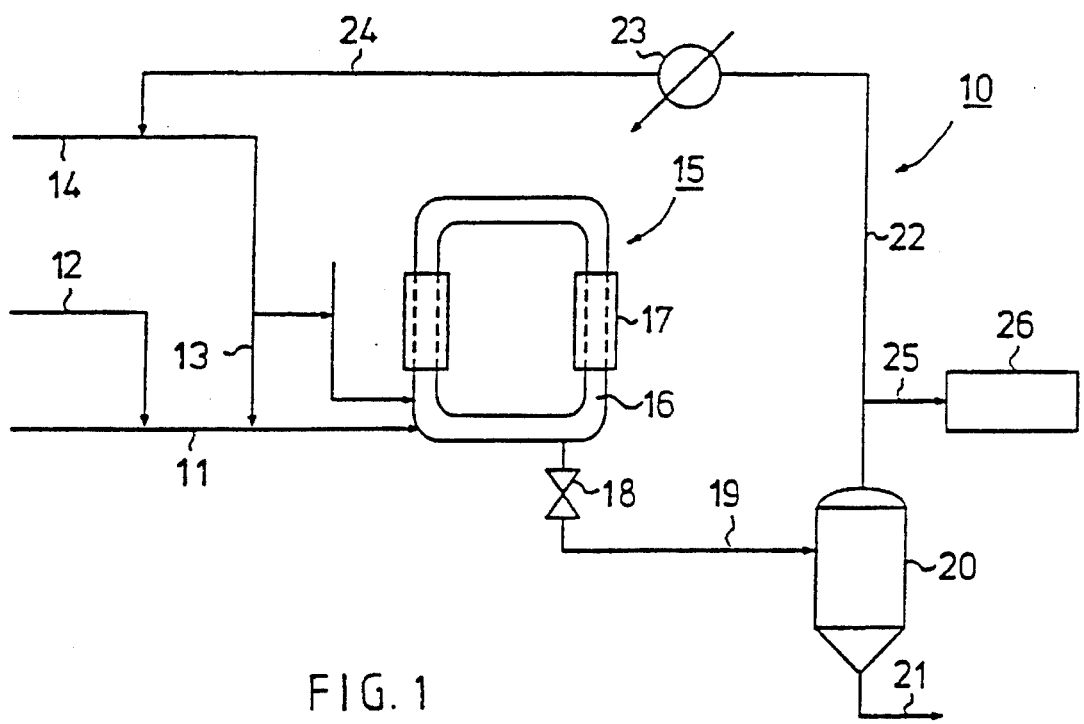
FIG. 1 is a schematic illustration of a conventional prior-an loop-reactor system.

In FIG. 1 (prior art), the reference numeral 10 represents a polymerization equipment, in which, through a feed pipe 11, a monomer is passed from the pipe 12, a catalyst from the pipe 13, and a diluent from the pipe 14 into the loop reactor 15. In the reactor 15 pipe 16, the suspension consisting of the reaction agents and of the polymer that is being formed is circulated at a high velocity by means of a circulation equipment not shown, such as a pump or a propeller device. The temperature in the reactor 15 can be regulated by means of a heating/cooling mantle 17. The above system of feed of the reaction agents is just suggestive, and so the reaction agents can be passed into the reactor 15 in any desired way whatsoever, together or separately.

Out of the reactor 15, the suspension consisting of polymer, diluent, and monomer is removed through the valve 18. The valve 18 is opened periodically for a short time, for example, at intervals of half a minute, and allows product suspension to pass through the pipe 19 into the separation tank 20. In the separation tank 20, owing to the lowering of the pressure, the diluent contained in the suspension is gasified, the solid polymer product being removed through the pipe 21, and the gaseous phase which contains diluent and monomer is removed through the pipe 22, and said phase can be returned into the reactor 15 along the pipe 24 after its pressure has been increased in a compressor 23.

Out of the pipe 22, through the pipe 25, a gas sample can be taken to the analyzer 26. Since the volume of the separator 20 is considerably large and since the product flow into the separator is periodic, adequate mixing of the gas phase and formation of a representative sample take a considerable length of time, which may be up to 15 minutes. Thus, this causes a considerable delay in the analysis.

Figure 2:
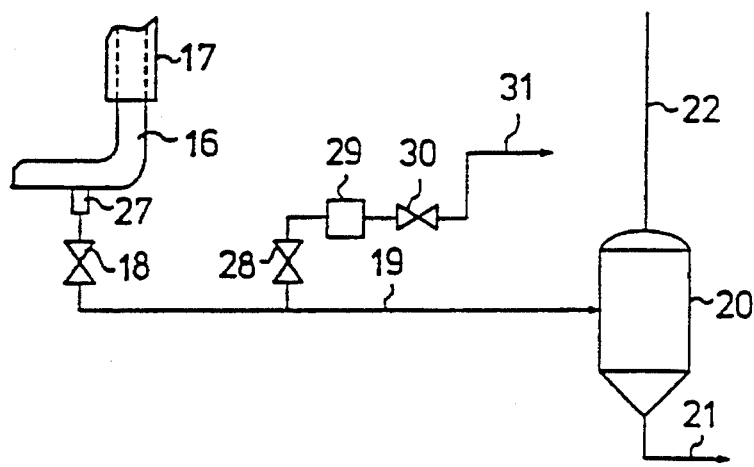
FIG. 2 is a schematic illustration of a prior-an sampling system in accordance with the FI Patent 85,191.

FIG. 2 (prior art) shows a sampling system in accordance with the FI Patent 85,191, wherein the sample is taken from the reactor 15 through the duct 27 and the exhaust valve 18 relatively soon directly from the product pipe 19 through the valve 28 into the pipe 31 passing to the analyzer, through a constant-flow valve 30.

When the exhaust valve 18 is opened, the pressure of the reactor 15 has access directly into the product pipe 19, and this produces a considerable pressure shock. This pressure shock must not have access to the analyzers, and therefore the valve 28 that is used is a valve of the on/off type, which valve is closed when the exhaust valve 18 is opened, for the time of the maximum pressure swing. The duration of the pressure swing is of an order of 5 seconds. After the pressure swing, the valve 28 is opened and allows the sample to flow to the analyzer through the valve 30 and the pipe 31.

In order that the sample flow to the analyzer should be continuous, after the valve 28 a buffer tank 29 is provided, whose volume has been measured such that it is sufficient to guarantee that the flow through the pipe 31 is continuous even if the valve 28 is closed in between.

Figure 3:
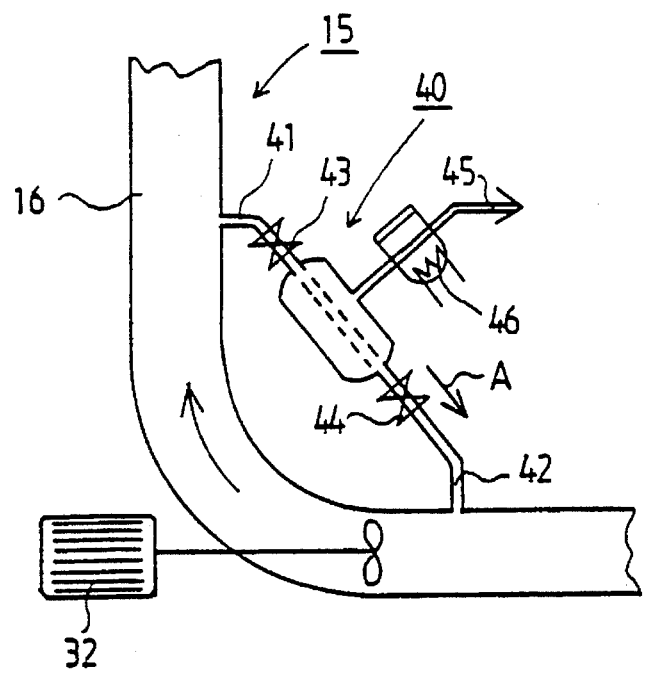
FIG. 3 is a schematic illustration of a preferred embodiment of the sampling method in accordance with the present invention.

In the embodiment as shown in FIG. 3, the taking of a sample takes place in accordance with the basic realization of the invention directly in the liquid phase of the reactor 15 by means of an in-line filter 40. One end of the filter 40 communicates with the pipe 16 of the loop reactor 15 through the flow duct 41, and the other end of the filter 40 through the flow duct 42. The flow duct 41 includes a valve 43, and the flow duct 42 includes a valve 44. The sample is passed from the filter 40 through the duct 45 to gas-chromatographic analysis. The reference numeral 46 represents a vaporizer and pressure reducer. The sample flows from the pipe 16 of the loop reactor 15 through the pipe 41, through the in-line filter 40, and through the pipe 42 in the direction indicated by the arrow A at a very high velocity. A suitable velocity is, as a rule, 3 . . . 10 metres per second. The circulation equipment placed in the pipe 16 of the loop reactor 15 is denoted with the reference numeral 32.

Figure 4:
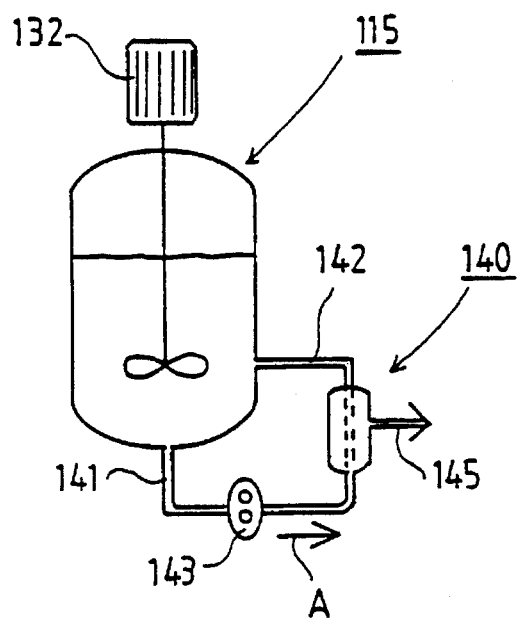
FIG. 4 is a schematic illustration of a second preferred embodiment of the sampling method in accordance with the invention.

In the embodiment as shown in FIG. 4, one end of the in-line filter 140 communicates with the slurry tank reactor 115 through the flow duct 141, and the other end of the filter through the duct 142. The flow duct 141 includes a slurry pump 143. The sample is passed from the filter 140 along the flow duct 145 to gas-chromatographic analysis. The agitator device placed in the slurry tank reactor 115 is denoted with the reference numeral 132.

We claim:

1. Method for taking a sample from the liquid phase of a loop reactor (15) in slurry polymerization through an in-line filter (40) placed in the liquid phase flow of the reactor, characterized in that the slurry flow across the in-line filter (40) is maintained at a sufficiently high level to prevent immobilization of polymer or catalyst particles on the filter face of the in-line filter (40) utilizing the pressure difference produced by a circulating pump (32) of the loop reactor (15).

2. Equipment for taking a sample from a loop reactor (15) in slurry polymerization, characterized in that the equipment comprises an in-line filter (40) which communicates with the slurry, which flows in a pipe (16) of the loop reactor (15), through a first flow duct (41) at one end thereof and through a second flow duct (42) at the other end thereof, and that the first flow duct (41) communicates with the pressure side of a circulating pump (32) of the loop reactor (15) and the other flow duct (42) communicates with the suction side of the circulating pump (32) of the loop reactor (15).

3. Equipment as claimed in claim 2, characterized in that the first flow duct (41) is provided with a valve (43) and the second flow duct (42) is provided with a valve (44), and that the in-line filter (40) communicates through a duct (45) with gas-chromatographic analysis.

* * * * *